United States Patent [19]
Winston et al.

[11] Patent Number: 5,350,377
[45] Date of Patent: Sep. 27, 1994

[54] MEDICAL CATHETER USING OPTICAL FIBERS THAT TRANSMIT BOTH LASER ENERGY AND ULTRASONIC IMAGING SIGNALS

[75] Inventors: Thomas R. Winston, Leawood; John M. Neet, Shawnee, both of Kans.

[73] Assignee: Ultrasonic Sensing & Monitoring Systems, Inc., Leawood, Kans.

[21] Appl. No.: 966,279

[22] Filed: Oct. 26, 1992

[51] Int. Cl.⁵ .................... A61B 17/36; A61B 8/12
[52] U.S. Cl. ................................ 606/15; 606/13; 607/89; 128/660.01
[58] Field of Search ......... 128/660.01, 660.03–660.07, 128/662, 03, 662, 06, 395–398; 606/2, 7, 8, 10–16; 335/25, 26, 90, 92

[56] References Cited
U.S. PATENT DOCUMENTS

| | | | |
|---|---|---|---|
| 4,887,605 | 12/1989 | Angelsen et al. | 606/7 |
| 5,010,886 | 4/1991 | Passafaro et al. | 128/662.06 |
| 5,029,588 | 7/1991 | Yock et al. | 606/7 |
| 5,152,291 | 10/1992 | Das | 128/662.06 |

*Primary Examiner*—Stephen C. Pellegrino
*Assistant Examiner*—M. Peffley
*Attorney, Agent, or Firm*—Hovey, Williams, Timmons & Collins

[57] ABSTRACT

A medical catheter which includes one or more optical fibers, each of which transmits both ultrasonic signals for imaging of the treatment area and laser energy for treatment of a medical condition. Different embodiments of the invention make use of different ways to utilize the same fiber for both ultrasonic and laser transmission.

10 Claims, 3 Drawing Sheets

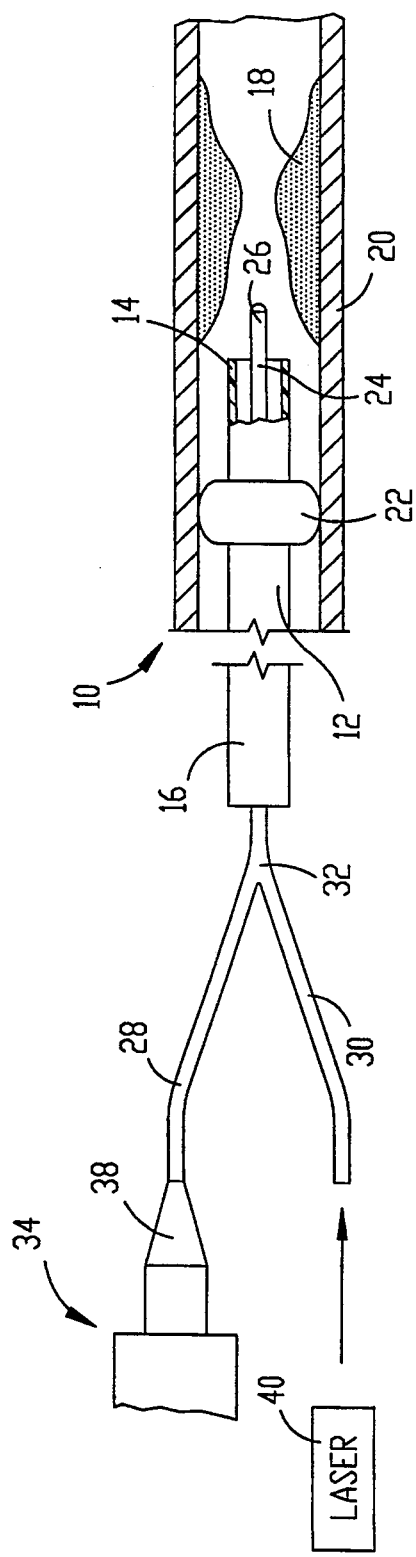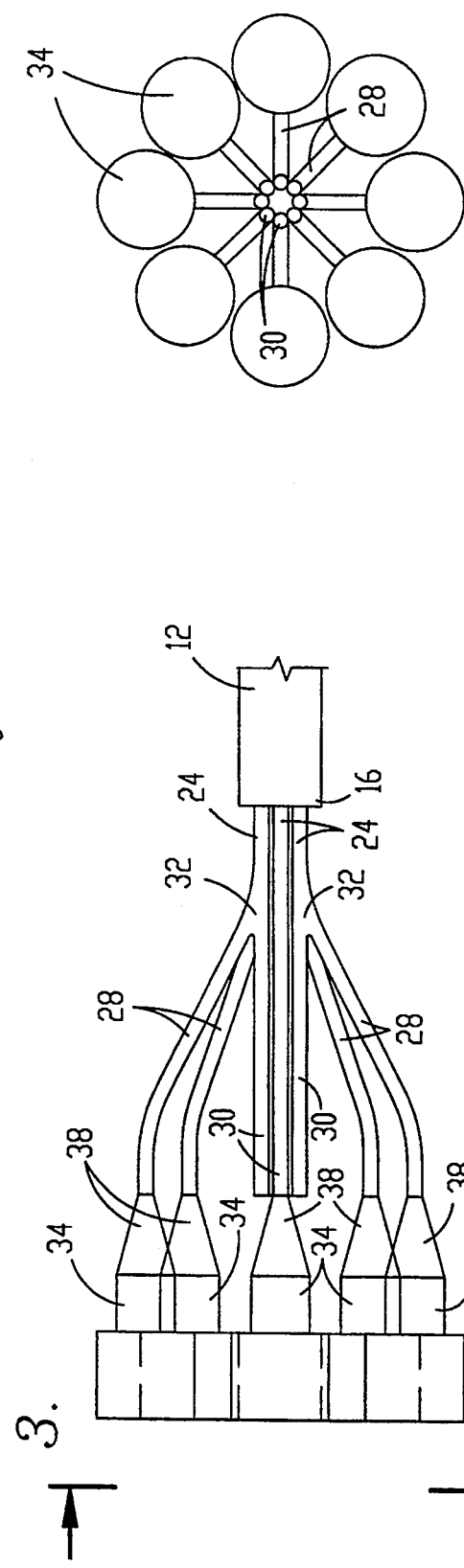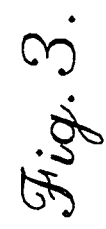

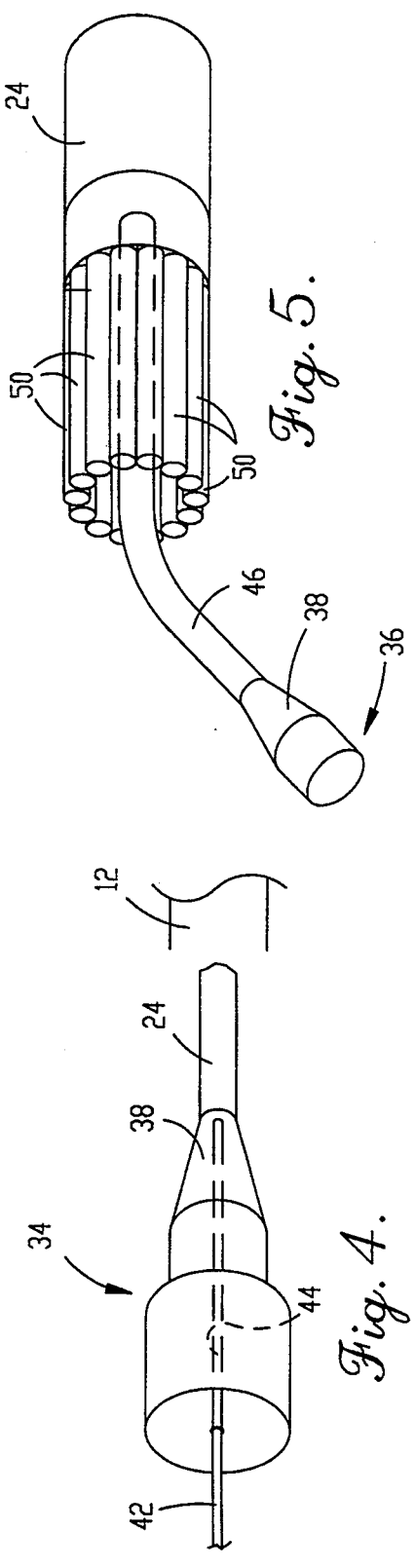
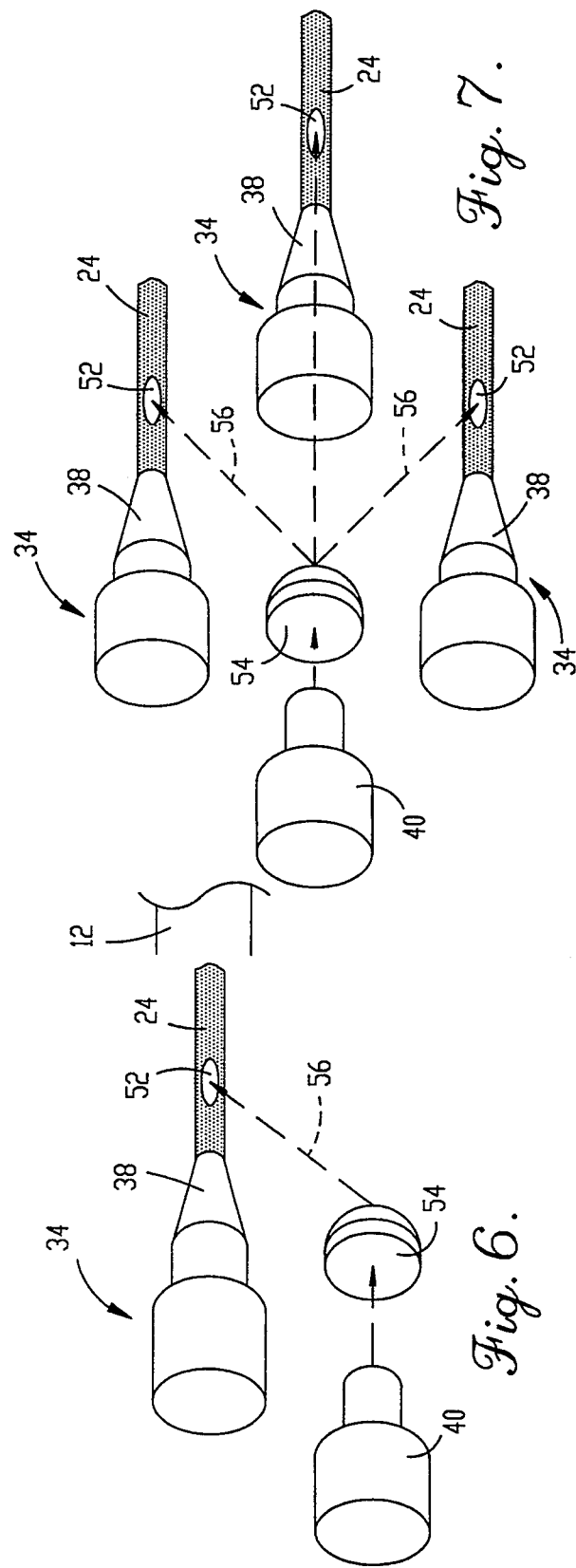

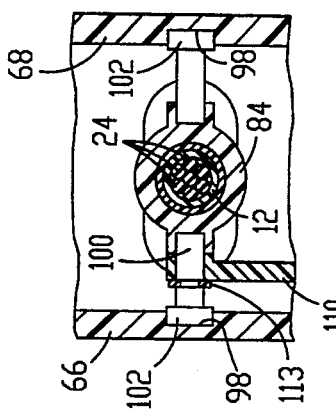
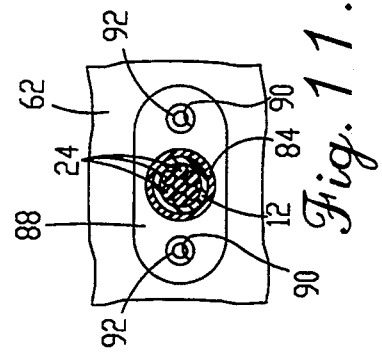
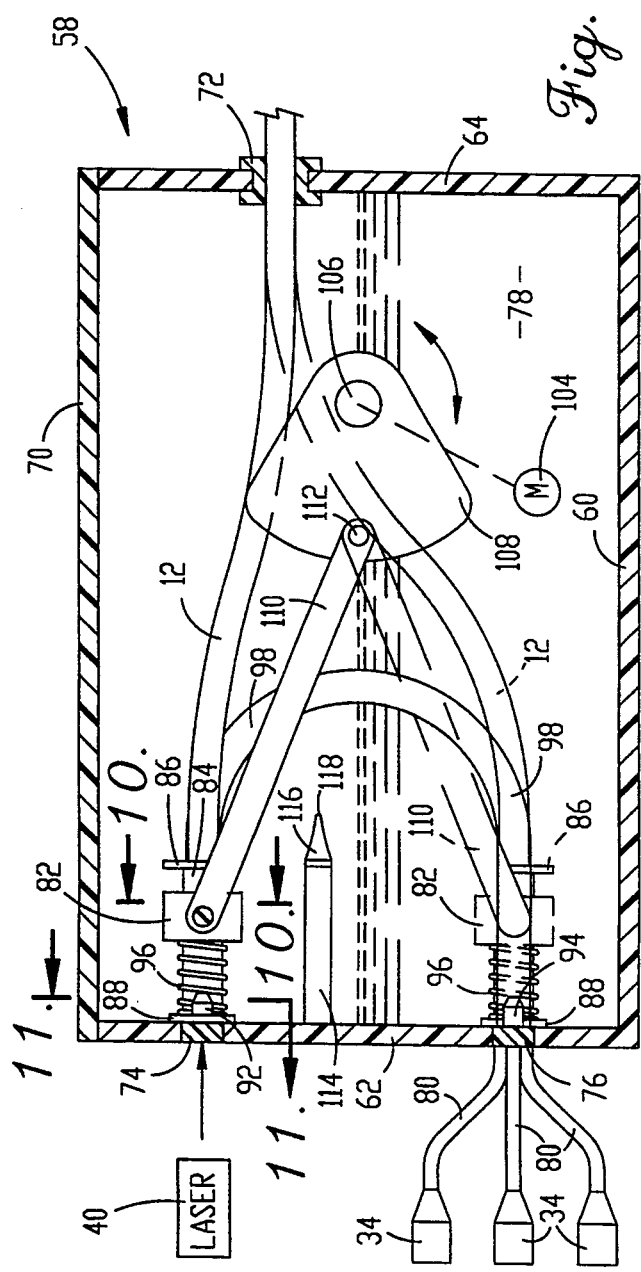
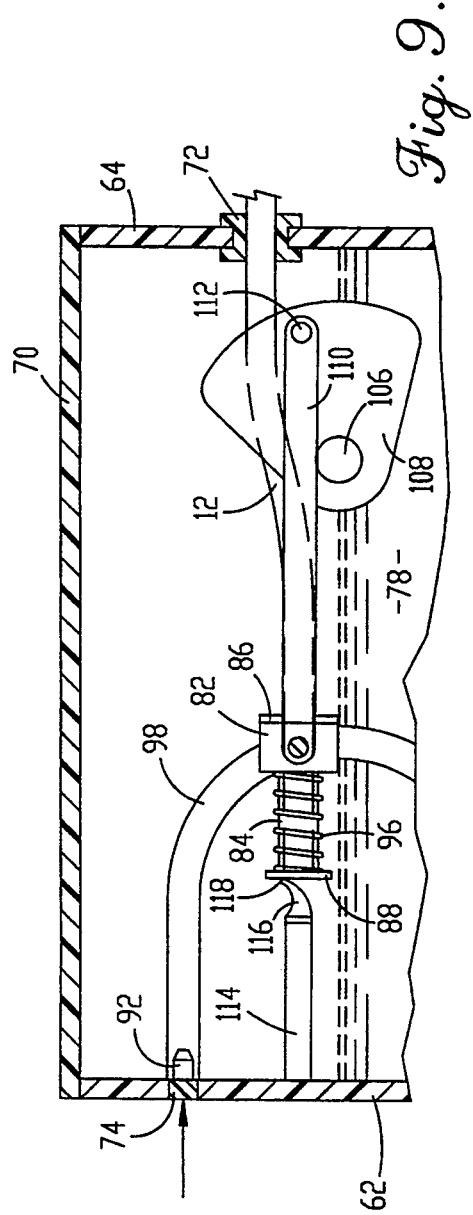

MEDICAL CATHETER USING OPTICAL FIBERS THAT TRANSMIT BOTH LASER ENERGY AND ULTRASONIC IMAGING SIGNALS

FIELD OF THE INVENTION

This invention relates in general to medical laser treatment of atherosclerotic plaque and other conditions. The invention deals more particularly with a method and apparatus that makes use of a catheter equipped with optical fibers, each of which transmits both ultrasonic imaging signals and laser energy for treatment of the medical condition.

BACKGROUND OF THE INVENTION

Lasers have been used in a variety of medical applications, including the treatment of atherosclerotic plaque which builds up on the walls of arteries and can create cardiovascular problems by restricting arterial flow. In order to properly apply the laser energy, it is necessary to obtain an image of the area that is to undergo treatment. For example, U.S. Pat. No. 4,576,177 to Webster discloses a catheter which includes optical fibers for transmitting laser energy and an ultrasonic transducer at the tip end of the catheter for obtaining ultrasonic images. Electrical wires extend through the catheter to provide power for operating the ultrasonic transducer and to transmit image information sensed by the transducer.

Pending application Ser. No. 672,822 filed on Mar. 21, 1991 in the name of Thomas R. Winston for "Catheter for Laser Treatment of Atherosclerotic Plaque and other Abnormalities" discloses a number of different catheter constructions that improve upon the catheter shown in the Webster patent. Pending application Ser. No. 824,023 filed on Jan. 22, 1992 in the names of Thomas R. Winston and John M. Neet for "Medical Catheter Using Ultrasound Mapping With External Transducers" discloses yet another improvement in which the ultrasonic transducer is external to the catheter.

In the arrangement shown in the latter application, separate optical fibers are used to transmit the ultrasonic signals and the laser energy. While this is entirely satisfactory in some applications, there are other applications in which the need to provide separate fibers for the ultrasound and laser energy is a significant disadvantage.

SUMMARY OF THE INVENTION

The present invention is directed to an improved medical catheter in which one or more optical fibers are extended through a catheter, and each fiber transmits both ultrasonic signals used for ultrasonic imaging and laser energy used for treating the medical problem (arterial plaque build up, for example). The catheter may have a single fiber, multiple fibers arranged in a bundle, or multiple fibers arranged in multiple bundles. In all cases, each fiber is connected both to an ultrasonic transducer and to a laser so that it transmits the energy used for the ultrasonic imaging as well as the energy used for laser treatment.

In accordance with the invention, different arrangements may be provided to allow the same fiber to transmit both ultrasound and laser energy. In one form of the invention, a Y-shaped fiber coupler having two branches connects to the optical fiber which extends through the catheter. The ultrasonic transducer can be connected to one of the branches and the laser can be connected to the other branch. A modified way of using this same concept provides multiple fibers extending through the catheter, with each fiber having two branches for accommodating both ultrasound and laser energy.

In another form of the invention, the ultrasonic transducer is connected to the optical fiber and another smaller fiber passes through the transducer and connects with the main fiber. The laser energy can be applied to the smaller fiber and is transmitted from it to the main fiber and ultimately to the area that is undergoing treatment.

In another embodiment of the invention, the ultrasonic transducer is connected with an optical filament that is smaller than the main fiber and which connects with the main fiber by means of a suitable coupler. A plurality of additional small filaments are arranged in a circle around the filament which transmits ultrasound, and these additional filaments are likewise coupled with the main optical fiber. By means of this arrangement, both the ultrasound and laser energy can be applied to the same main fiber, the ultrasound making use of the central filament and the laser energy being applied to the other filaments.

In still another form of the invention, the transducer connects with the optical fiber, and the laser energy is applied to the fiber through an area on the surface of the fiber which is devoid of optical coating. Plural fibers can be extended through the catheter if desired, with each fiber having an ultrasonic transducer and the laser energy being applied to each fiber by means of a beam splitter which directs the laser energy to the uncoated area on each fiber.

Yet another embodiment of the invention includes a panel which may be an end panel on a tank containing a suitable fluid. The panel is provided with a window for receiving the laser energy and a port that connects with one or more ultrasonic transducers. The catheter may contain one or more optical fibers, and the input end of the catheter can be moved between the window and the port so that both ultrasound and laser energy can be applied to the fiber or fibers which extend through the catheter. A track is provided to guide the catheter between the window and port. A motor is provided to move the catheter by means of a linkage that is arranged to transport the input end of the catheter along the path that is defined by the track. Alignment pins assure precise positioning of the catheter end with respect to both the window and the port. Preferably, the port is immersed in the liquid contained by the tank, and a wiper arrangement may be provided to wipe the end of the fiber or fibers as they move out of the liquid toward the window at which laser energy is to be applied.

DESCRIPTION OF THE DRAWINGS

In the accompanying drawings which form a part of the specification and are to be read in conjunction therewith and in which like reference numerals are used to indicate like parts in the various views:

FIG. 1 is a diagrammatic side elevational view of a catheter constructed according to one embodiment of the present invention, with the break lines indicating continuous length and the catheter shown inserted with its tip end in position to effect treatment of an arterial plaque deposit;

FIG. 2 is a diagrammatic side elevational view of a catheter which is similar to that shown in FIG. 1 but which includes a plurality of different optical fibers each of which transmits both ultrasound and laser energy;

FIG. 3 is a fragmentary end elevational view taken generally along line 3—3 of FIG. 2 in the direction of the arrows;

FIG. 4 is a fragmentary perspective view of a catheter constructed according to a modified embodiment of the invention;

FIG. 5 is a fragmentary perspective view of a catheter constructed according to still another modified embodiment of the invention;

FIG. 6 is a fragmentary diagrammatic view of a catheter constructed according to yet another modified embodiment of the invention;

FIG. 7 is a fragmentary diagrammatic view of a catheter constructed according to still another embodiment of the invention;

FIG. 8 is a fragmentary diagrammatic view of a catheter constructed according to yet another embodiment of the invention, with the solid line showing the input end of the catheter positioned adjacent a window to receive laser energy and the broken lines showing the input end of the catheter positioned adjacent to a port for receiving ultrasound;

FIG. 9 is a fragmentary diagrammatic view similar to FIG. 8, but showing the input end of the catheter positioned about midway between the port and the window and being wiped by a wiper;

FIG. 10 is a fragmentary sectional view on an enlarged scale taken generally along line 10—10 of FIG. 8 in the direction of the arrows; and FIG. 11 is a fragmentary sectional view taken generally along line 11—11 of FIG. 8 in the direction of the arrows.

DETAILED DESCRIPTION OF THE INVENTION

Referring now to the drawings in more detail and initially to FIG. 1, a catheter which is constructed according to one embodiment of the present invention is generally identified by numeral 10. The catheter 10 includes an elongated flexible catheter tube 12 which is hollow and preferably circular in cross-section. The catheter tube 12 is constructed in a suitable manner to be inserted into the body with one end 14 situated adjacent to the area that is to be treated and the other end 16 remaining external of the body. By way of example, FIG. 1 depicts use of the catheter 10 in the treatment of atherosclerotic plaque 18 which has built up on the wall of an artery 20. In this type of application, the distal end 14 of the catheter tube 12 is inserted into the artery 20 to the location of the plaque deposit 18. An annular seal 22 may be provided near the distal end 14 to effect a seal between the outside of the catheter tube 12 and the arterial wall.

An optical fiber 24 extends through the catheter tube 12 and terminates in a tip 26 which may project out through the distal end 14 of the catheter tube. The opposite or input end of the optical fiber 24 suitably connects with a Y-shaped fiber coupler having two branches 28 and 30 that merge at a junction 32. The fiber coupler is a commercially available article, and it may be fused or otherwise suitably connected end to end with the main optical fiber 24. The fiber 24 and the fiber coupler may be quartz or silicon fiber coated with an external reflective material.

A conventional ultrasonic transducer 34 is located outside of the catheter tube 12 and is excited electrically in the usual manner to transmit ultrasonic signals through a piezo-electrode. The transducer 34 connects with the free end of branch 28 through a tapered transition element 38. The ultrasonic signals which are transmitted to the transition element 38 by the transducer are transmitted along the branch 28 to the fiber 24 and are directed to the area that is to undergo treatment through the fiber tip 26. Pulse echoes which are reflections of the transmitted signals are received by the tip 26 and are transmitted along the fiber 24 and the branch 28 back to the transducer. The transducer transforms the received pulse echoes into electrical signals which provide data to form an image of the area that is to undergo treatment. In this fashion, the ultrasonic system provides images as to the configuration, location and character of the tissue in the area of the plaque 18. Preferably, the transducer is a piezo-electric ceramic crystal unit.

The tapered transition element 38 may be a solid frusto-conical member constructed of a substance suitable to conduct ultrasonic signals. As an alternative, the transition element 38 may take the form of a hollow frusto-conical member that is filled with a fluid capable of conducting ultrasonic signals. The large end of the transition element 38 connects with the piezo-electrode 36, and the small end connects with the free end of the branch 28.

Laser energy is applied to the free end of the other branch 30 by a medical laser 40. The laser energy is applied to the branch 30 and is transmitted along the branch and the fiber 24 to the tip 26 which directs the laser energy toward the plaque 18 in order to remove the plaque 18 or at least reduce the plaque build up.

FIGS. 2 and 3 depict an alternative embodiment of the invention in which the catheter tube 12 contains a plurality of the optical fibers 24. Each of the fibers 24 is fused or otherwise connected at its proximal end with a fiber coupler having a pair of branches 28 and 30. The branches 28 connect with respective transducers 34 via transition elements 38. Consequently, each of the fibers 24 receives ultrasonic signals from the corresponding transducer 34 and transmits reflected pulse echoes back to the corresponding transducer 34. In this fashion, the plural transducers 34 provide accurate ultrasonic imaging information of the area that is to undergo treatment.

The fibers 24 may be arranged in a circular pattern, and the branches 30 may be arranged in line with the respective fibers 24 such that the branches 30 are essentially in line extensions of the fibers. The extensions 30 are thus arranged in a circular pattern, as best shown in FIG. 3. The laser 40 may be used to apply laser energy to the free ends of the extensions 30, and the extensions and fibers 24 transmit the laser energy through the catheter tube 12 to the area undergoing treatment. Because of the circular arrangement of the fibers 24, the transducers 34 may be arranged in a circular pattern, as shown in FIG. 3.

FIG. 4 depicts another modified embodiment of the invention in which the transition element 38 is fused or otherwise connected directly to the proximal end of the fiber 24. The transducer 34 applies ultrasonic signals to the fiber 24 through the transition element 38 in the manner previously described, and the pulse echoes are transmitted back to the transducer in the same fashion described previously as well.

The laser 40 applies laser energy to a small optical fiber or filament 42. The filament 42 may take the form of an optical fiber having a construction similar to that of the fiber 24 but a diameter considerably less than that of the fiber 24. The filament 42 extends through a passage 44 which is formed through the transducer 34 and transition element 38. The end of the filament 42 butts against the input end of the fiber 24 and is fused or otherwise Suitably connected with the optical fiber. The laser energy which is applied to the filament 42 is thus applied to the input end of the optical fiber 24 and is transmitted along the optical fiber and applied to treat the medical problem that is undergoing treatment.

FIG. 5 depicts an alternative embodiment of the invention in which the transition element 38 connects with one end of an optical fiber or filament 46. The piezo-electrode of the transducer 34 is connected to the transition element 38 as previously described. The opposite end of the filament 46 extends to and connects with the proximal end of the optical fiber 24. The filament 46 may be constructed in a manner similar to the fiber 24, but filament 46 is considerably smaller in diameter than the fiber 24. The end of the fiber 46 is fused or otherwise suitably connected with the end of the fiber 24.

The transducer 34 applies ultrasonic signals to filament 46 which in turn applies the signals to the fiber 24. The pulse echoes are transmitted back to the transducer to provide ultrasonic imaging data of the area that is to undergo treatment.

A plurality of additional filaments 50 connect with the proximal end of fiber 24 (as by fusing, for example) and may be arranged in a circular pattern around the filament 46. The filaments 50 may be larger or smaller than the central filament 46, and they may be constructed in a manner similar to the fiber 24. However, the filaments 50 are preferably somewhat smaller in diameter than the central filament 46. The laser 40 operates to apply laser energy to the filaments 50, and the laser energy is transmitted along the filaments 50 to the fiber 24 which transmits the laser energy along it and applies the laser energy to the area that is undergoing treatment.

FIG. 6 depicts yet another alternative embodiment of the invention in which the transition element 38 is connected with the proximal end of the fiber 24. The transducer 34 operates in the same manner described previously to provide ultrasonic imaging data of the area that is to undergo treatment. As previously described, the exterior of the fiber 24 is provided with an optical coating. In the embodiment shown in FIG. 6, a small area 52 on the surface of the fiber 24 is devoid of the optical coating, thus providing a small "window" through which laser energy is able to enter the fiber 24 and thereafter propagate along the length of the optical fiber for application to the area undergoing treatment. The laser 40 applies laser energy through a beam splitter 54 which directs the laser energy in a beam 56 toward the window area 52 on the surface of the fiber 24. In this manner, the laser energy is applied to the fiber 24 and is transmitted along the fiber to treat the afflicted area. If necessary, measures can be taken to assure that the laser energy propogates away from the transducer.

FIG. 7 depicts an embodiment of the invention which is similar to that depicted in FIG. 6, the difference being that in the FIG. 7 embodiment a plurality of the fibers 24 extend through the catheter tube 12, with each fiber 24 equipped with a transducer 34. The laser 40 applies laser energy to the beam splitter 54, and the beam splitter splits the laser energy into separate beams 56 which are applied to the window areas 52 of the respective fibers 24. Consequently, laser energy is applied to each of the fibers 24 and is transmitted along the fibers and applied to the afflicted area at the distal end of the catheter tube. The beam splitter can operate to direct the beams 56 to only those fibers that require laser energy for treatment of the condition that is indicated by the ultrasonic information.

FIGS. 8—11 depict yet another embodiment of the invention in which the part of the catheter tube near the proximal end 16 extends within a tank 58. The tank 58 has a flat bottom 60 opposite end panels 62 and 64 and opposite side walls 66 and 68 (see FIG. 10). A removable cover 70 fits on top of the tank 58. The catheter 12 extends through the end panel 64 and is sealed to panel 64 by a seal element 72.

With particular reference to FIG. 8, the end panel 62 is provided with a window 74 located near its top end and with a port 76 located near its bottom end below the level of the window 74. The laser 40 can be operated to apply laser energy to the window 74 and through the window to a plurality of optical fibers 24 contained in the catheter tube 12. The port 76 is located below the level of a liquid 78 which is contained within the tank 58. The liquid 78 may be glycerin, water or another liquid that is able to transmit ultrasound. Connected with the port 76 are a plurality of transducers 34, each of which has an optical fiber 80 extending from it to the port 76. When the catheter tube 12 is connected with the port 76, ultrasound signals are transmitted from the transducers 34 along the fibers 80 to the port 76 and from the port to the optical fibers 24 which extend within the catheter tube 12. Return pulse echoes are transmitted along the fibers 24 to the port 76 and from the port to the transducers 34 along fibers 80. The fibers 80 may be surrounded by a suitable sealant which seals them to port 76 to make the port liquid tight.

The proximal end of the catheter tube 12 is transferred between the window 74 and the port 76 by a mechanism which includes a carriage in the form of a collar 82 which is sleeved on a spool 84 fixed to the proximal end 16 of the catheter tube 12. The collar 82 fits slidably on the spool 84. One end of the spool 84 is provided with a flange 86 which limits movement of the collar on the spool in one direction. The opposite end of the spool 84 is provided with an end plate 88 having a pair of alignment openings 90 (see FIG. 11) located on opposite sides of the catheter tube 12. A pair of alignment pins 92 project inwardly from panel 62 on opposite sides of the window 74 and are positioned to receive the openings 90 in order to properly align the catheter tube with the window 74. Another pair of alignment pins 94 project from panel 62 on opposite sides of the port 76. When the catheter tube 12 is applied to the port 76, the alignment pins 94 receive the alignment openings 90 in order to assure that the catheter tube 12 is properly aligned with the port 76. A compression spring 96 is coiled around the spool 84 and acts against plate 88 at one end and against the collar 82 at the other end, thereby urging the end plate 80 and collar 82 apart.

The collar 82 travels along a prescribed path defined by a pair of curved tracks 98 which are formed in the side walls 66 and 68 of tank 58. As shown in FIG. 10, the collar 82 is equipped with a pair of shafts 100 which project from the collar on opposite sides. Carried on the outer ends of the shafts 100 are guide elements 102 which fit closely in the tracks 98. By reason of the guide elements 102 traveling along the tracks 98, the collar 82 is guided along the path defined by the tracks 98 in order to guide the catheter end between one position in which it is aligned with window 74 and another position in which it is aligned with port 76.

Movement of the collar 82 is effected by a conventional electric motor 104 (FIG. 8) which drives an output shaft 106. Carried on the shaft 106 is an eccentric or a cam 108. One end of a rigid link 110 is pinned at 112 to the cam 108 at a location offset from the shaft 106. The opposite end of the link 110 is pivoted to one of the shafts 100 and retained on the shaft by a retaining element 113.

Extending inwardly from panel 62 at a location between the window 74 and port 76 is an arm 114. Carried on the free end of the arm 114 is a suitable wiping element 116 which may take the form of a wiping blade tapering down to a wiping edge 118. The location of the wiping element 116 is such that it is contacted by the end of the catheter tube 12 and the ends of the fibers 24 as the catheter tube is moved between its two different positions. When the catheter tube is moved from the port 76 toward the window 74, the ends of the fibers 24 are wiped of the liquid 78. Preferably, the wiping element 116 is located a short distance above the level of the liquid 78.

The embodiment of the invention shown in FIGS. 8-12 operates to provide ultrasonic imaging of the area that is to undergo treatment and to effect the treatment via laser energy applied by the laser 40. When the catheter tube 12 is positioned against the port 76, ultrasonic signals are applied to the fibers 24 through the window, and pulse echoes are applied back from the fibers 24 through the window 76 to the ultrasonic transducers 34. In this manner, ultrasonic images of the area that is to undergo treatment are obtained.

When the laser treatment is to be carried out, the catheter tube 12 is moved from the lower position in which it is aligned with the port 76 to the upper position in which it is aligned with the window 74. Movement of the catheter tube is carried out by operating the motor 104 in a direction causing the cam 108 to rotate one revolution in a counterclockwise direction. As the cam rotates, the link 110 pulls on collar 82, and the collar acts against flange 86 to pull the spool 84 in a direction away from the port 76. The guide elements 102 follow the tracks 98. When the cam has rotated through half a revolution, the collar 82 is located approximately midway along the track 98. Continued rotation of the cam causes the link 108 to begin pushing the collar, and this pushing force is transmitted through spring 96 to the end plate 88. As the cam approaches the end of its revolution, the alignment pins 92 receive the openings 90 to assure that the end of the catheter tube 12 is aligned precisely with the window 74. The spring 96 is compressed in order to press the end plate 88 securely against the end panel 62 to assure that the end of the catheter 12 is held against the window 74. Laser energy can then be applied to some or all of the fibers 24 through window 74 to carry out the laser treatment of the medical problem.

As best shown in FIG. 9, the end of the catheter tube 12 and the fibers 24 are wiped clear of the liquid 78 as the end of the catheter emerges from the liquid. The end of the catheter is swept across the wiping element 118 which acts to remove any liquid that may be present on the fibers. Consequently, the fibers are clear of liquid when the catheter tube is positioned against the window 74.

In order to move the catheter tube again to the lower position, the cam 108 is rotated one revolution in a clockwise direction. The guiding action provided by the guide elements 108 and tracks 98 carries the catheter tube from the window 74 to the port 76. As the end of the catheter tube approaches the port 76, the alignment pins 94 receive the alignment openings 90 to assure that the end of the catheter tube is precisely aligned with the port 76. The spring 96 is compressed, and this presses the end plate 88 against panel 62 to assure that the end of the catheter tube is held against the port 76.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A catheter for insertion into the body to effect medical treatment, comprising:
    an elongated catheter tube having opposite ends;
    an optical fiber extending through said catheter tube and terminating in a tip disposed in the body when the catheter tube is inserted therein, said optical fiber having an input end opposite the tip;
    a panel adjacent said input end of said optical fiber;
    a port on said panel;
    ultrasonic transducer means connected to said port for applying ultrasonic signals to said input end of the fiber for transmission therealong to said tip and for receiving reflected ultrasonic signals received by said tip and transmitted along said fiber to said input end, thereby providing ultrasonic information regarding the treatment area adjacent the fiber tip;
    a window on said panel at a location thereon spaced from said port;
    means for applying laser energy through said window to said input end of the fiber to effect treatment of the area adjacent the fiber tip; and
    means for effecting selective movement of said input end of the fiber between a first position adjacent said window for the receipt of laser energy and a second position adjacent said port for the receipt of said ultrasonic signals and the reflected signals.

2. The catheter of claim 1, including cooperating alignment pin and alignment hole means on said panel and catheter tube to assure alignment of the input end of said fiber with said window in said first position and with said port in said second position.

3. The catheter of claim 1, including spring means for urging said input end of the fiber against said window in said first position and against said port in said second position.

4. The catheter of claim 1, including: a carriage on said catheter tube;
- means for guiding said carriage along a prescribed path relative to said panel carrying said input end of the fiber between said first and second positions; and
- power means connected to said carriage for driving said carriage along said prescribed path.

5. The catheter of claim 4, wherein:
- said panel is located on a tank having opposite sides and adapted to hold a liquid in which said port is immersed.

6. The catheter of claim 5, including means disposed along the prescribed path for wiping liquid from said input end of the fiber during travel thereof from the second position toward the first position.

7. The catheter of claim 5, wherein:
- said guide means comprises tracks on said sides of the tank defining said prescribed path and guide elements on said carriage constrained to follow said tracks.

8. The catheter of claim 7, wherein said power means comprises:
- a power element driving an output shaft;
- a cam mounted on said shaft; and
- a link coupling said cam with said carriage in a manner to effect movement from the first position toward the second position when said shaft is rotated in one direction and from the second position toward the first position when said shaft is rotated in the opposite direction.

9. The catheter of claim 4, wherein:
- said carriage comprises a collar mounted on said catheter tube for limited sliding movement thereon;
- said catheter tube carries an end plate thereon; and
- said collar and end plate are urged apart by a compression spring acting therebetween in a manner to hold said end plate against said panel in the first and second positions.

10. The catheter of claim 9, including cooperating alignment pin and hole means on said panel and end plate to assure alignment of the input end of said fiber with said window in said first position and with said port in said second position.

* * * * *